(12) United States Patent
Ikari et al.

(10) Patent No.: US 6,232,343 B1
(45) Date of Patent: May 15, 2001

(54) OPHTHALMIC PREPARATIONS

(75) Inventors: Takashi Ikari, Yasu-gun; Yuzuru Matsumura, Gamo-gun; Tsutomu Nakamura, Kusatsu; Motoyuki Yajima, Urayasu; Hajimu Kurumatani, Kamakura; Ayako Kawashima, Fujisawa; Masafumi Isogaya, Yokohama; Hisanori Wakita, Chigasaki, all of (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 08/983,117

(22) PCT Filed: May 1, 1997

(86) PCT No.: PCT/JP97/01504

§ 371 Date: Mar. 9, 1998

§ 102(e) Date: Mar. 9, 1998

(87) PCT Pub. No.: WO97/41864

PCT Pub. Date: Nov. 13, 1997

(30) Foreign Application Priority Data

May 7, 1996 (JP) .................................................. 8-137697

(51) Int. Cl.$^7$ ........................ A61K 31/215; A61K 31/557
(52) U.S. Cl. ...................... 514/530; 514/573; 514/913
(58) Field of Search ................................. 514/530, 573, 514/913

(56) References Cited

U.S. PATENT DOCUMENTS 4,474,802 10/1984 Ohno et al. .
5,162,370 11/1992 Ueno .

FOREIGN PATENT DOCUMENTS

0469782A2 7/1991 (EP) .
54923 1/1993 (JP) .

OTHER PUBLICATIONS

Chemical Abstract 125: 67796 (1994)·Carst.*
Chemical Abstracts 125:213197·Hotechema, 1995.*

* cited by examiner

Primary Examiner—Zohreh Fay
(74) Attorney, Agent, or Firm—Birch, Stewart, Kolasch & Birch, LLP

(57) ABSTRACT

An ophthalmic preparation which exhibits excellent pharmacological effects for various ophthalmic diseases is disclosed. The ophthalmic preparation according to the present invention contains a 4,8-inter-m-phenylene prostaglandin I$_2$ derivative represented by the formula (I):

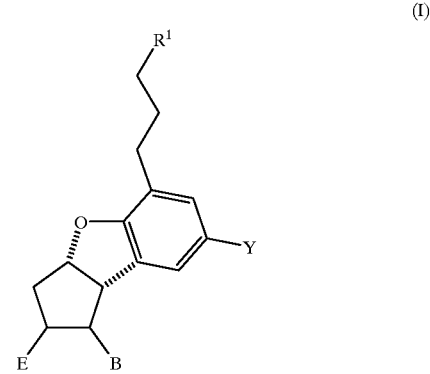

or a pharmaceutically acceptable salt thereof as an effective ingredient.

17 Claims, No Drawings

OPHTHALMIC PREPARATIONS

This application is the national phase under 35 U.S.C. §371 of prior PCT International Application No. PCT/JP97/01504 which has an International filing date of May 1, 1997 which designated the United States of America, the entire contents of which are hereby incorporated by reference.

TECHNICAL FIELD

The present invention relates to an ophthalmic preparation having an effect of decreasing ocular tension, which has a therapeutic and prevention effects against various ophthalmic diseases such as glaucoma, hypertonia oculi or cataract.

BACKGROUND ART

Beraprost (the general name of (±)-1R*, 2R*, 3aS*, 8bS*)-2,3,3a,8b-tetrahydro-2-hydroxy-1-[(E)-(3S* )-3-hydroxy-4-methyl-1-octene-6-ynyl]-1H-cyclopentane[b]benzofuran-5-butyric acid) is a stable derivative of prostaglandin $I_2$ ($PGI_2$) and has a wide variety of physiological actions such as strong antithrombotic activity and peripheral vasodilator action. Thus, beraprost has been attracting attention as a drug for improving peripheral circulatory disturbance.

However, application of beraprost to ophthalmic preparations has not been started. Research and development of application of beraprost to therapeutic agents of ophthalmic diseases, especially glaucoma, cataract and the like, is waited for.

DISCLOSURE OF THE INVENTION

An object of the present invention is to provide an ophthalmic preparation which exhibits excellent pharmacological effect against the above-mentioned ophthalmic diseases.

The present inventors discovered usefulness of beraprost and salts thereof as a therapeutic drug for glaucoma, hypertonia oculi, or postoperative hypertonia oculi by administering an ophthalmic preparation containing beraprost or a salt thereof, and discovered usefulness of the beraprost and salts thereof as a therapeutic drug for cataract by discovering the activity of beraprost to inhibit the swelling of crystalline lens and to inhibit the decrease of reduced glutathione in crystalline lens when crystalline lens is cultured with high concentration of galactose, thereby completing the present invention.

That is, the present invention provides an ophthalmic preparation comprising as an effective ingredient a 4,8-inter-m-phenylene prostaglandin $I_2$ derivative of the formula (I):

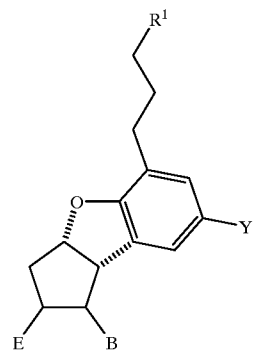

(I)

(wherein $R^1$ is
(A) $COOR^2$
(wherein $R^2$ is
1) hydrogen or a pharmaceutically acceptable cation,
2) $C_1$–$C_{12}$ straight alkyl or $C_3$–$C_{14}$ branched alkyl,
3) —Z—$R^3$
(wherein Z is a valence bond or straight or branched alkylene represented by $C_tH_{2t}$, wherein t is an integer of 1–6, $R^3$ is $C_3$–$C_{12}$ cycloalkyl or $C_3$–$C_{12}$ cycloalkyl substituted with 1 to 3 $R^4$ wherein $R^4$ is hydrogen or $C_1$–$C_5$ alkyl),
4) —($CH_2CH_2O$)$_n$$CH_3$
(wherein n is an integer of 1–5),
5) —Z—$Ar^1$
(wherein Z represents the same meaning as described above, $Ar^1$ is phenyl, α-naphthyl, β-naphthyl, 2-pyridyl, 3-pyridyl, 4-pyridyl, α-furyl, β-furyl, α-thienyl, β-thienyl or substituted phenyl (wherein the substituent is at least one selected from the group consisting of chlorine, bromine, fluorine, iodine, trifluoromethyl, $C_1$–$C_4$ alkyl, nitro, cyano, methoxy, phenyl, phenoxy, p-acetamidobenzamide, —CH=N—NH—C(=O)—$NH_2$, —NH—C(=O)—Ph, —NH—C(=O)—$CH_3$ and —NH—C(=O)—$NH_2$—,
6) —$C_tH_{2t}$$COOR^4$
(wherein $C_tH_{2t}$ and $R^4$ represent the same meanings as described above),
7) —$C_tH_{2t}$$N(R^4)_2$
(wherein $C_tH_{2t}$ and $R^4$ represent the same meanings as described above),
8) —CH($R^5$)—C(=O)—$R^6$
(wherein $R^5$ is hydrogen or benzoyl, $R^6$ is phenyl, p-bromophenyl, p-chlorophenyl, p-biphenyl, p-nitrophenyl, p-benzamidephenyl or 2-naphthyl),
9) —$C_pH_{2p}$—W—$R^7$
(wherein W is —CH=CH—, —CH=$CR^7$— or —C≡C—, $R^7$ is hydrogen, $C_1$–$C_{30}$ straight or branched alkyl or aralkyl, p is an integer of 1–5), or
10) —CH ($CH_2OR^8$)$_2$
(wherein $R^8$ is $C_1$–$C_{30}$ alkyl or acyl)
(B) —$CH_2OH$
(C)—C(=O)N($R^9$)$_2$
(wherein $R^9$ is hydrogen, $C_1$–$C_{12}$ straight alkyl, $C_3$–$C_{12}$ branched alkyl, $C_3$–$C_{12}$ cycloalkyl, $C_4$–$C_{13}$ cycloalkylalylene, phenyl, substituted phenyl (wherein the definition of the substituents are the same as (A)5) described above), $C_7$–$C_{12}$ aralkyl or —$SO_2R^{10}$, wherein $R^{10}$ is $C_1$–$C_{10}$ alkyl, $C_3$–$C_{12}$ cycloalkyl, phenyl, substituted phenyl (wherein the definition of the substituents are the same as (A)5) described above) or $C_7$–$C_{12}$ aralkyl, with the proviso that although the two $R^9$ may be the same or different, when one is —$SO_2R^{10}$, the other $R^9$ is not —$SO_2R^{10}$), or (D) —$CH_2OTHP$ (wherein THP represents tetrahydropyranyl), Y is hydrogen, $C_1$–$C_4$ alkyl, chlorine, bromine, fluorine, formyl, methoxy or nitro, B is —X—$C(R^{11})(R^{12})OR^{13}$ (wherein $R^{11}$ is hydrogen or $C_1$–$C_4$ alkyl, $R^{13}$ is hydrogen, $C_1$–$C_{14}$ acyl, $C_6$–$C_{15}$ aroyl, tetrahydropyranyl, tetrahydrofuranyl, 1-ethoxyethyl or t-butyl, X is
1) —$CH_2$—$CH_2$—
2) —CH=CH—, or
3) —C≡C—, $R^{12}$ is
1) $C_1$–$C_{12}$ straight alkyl or $C_3$–$C_{14}$ branched alkyl,
2) —Z—$Ar^2$ (wherein Z represents the same meaning as described above, $Ar^2$ represents phenyl, α-naphthyl, β-naphthyl or phenyl substituted with at least one selected from the group consisting of chlorine, bromine, fluorine, iodine, trifluoromethyl, $C_1$–$C_4$ alkyl, nitro, cyano, methoxy, phenyl and phenoxy), 3) —$C_tH_{2t}OR^{14}$ (wherein $C_tH_{2t}$ represents the same meaning as described above, $R^{14}$ is $C_1$–$C_6$ straight alkyl, $C_3$–$C_6$ branched alkyl, phenyl or substituted phenyl substituted with at least one selected from the group consisting of chlorine, bromine, fluorine, iodine, trifluoromethyl, $C_1$–$C_4$ alkyl, nitro, cyano, methoxy, phenyl and phenoxy, cyclopentyl, cyclohexyl, or cyclopentyl or cyclohexyl substituted with 1 to 4 $C_1$–$C_4$ straight alkyl),

4) —Z—$R^3$ (wherein Z and $R^3$ represent the same meanings as described above), 5) —$C_tH_{2t}$—CH=$C(R^{15})R^{16}$ (wherein $C_tH_{2t}$ represents the same meaning as described above, $R^{15}$ and $R^{16}$ independently represent hydrogen, methyl, ethyl, propyl or butyl), or 6) —$C_uH_{2u}$—C≡C—$R^{17}$ (wherein u is an integer of 1–7, $C_uH_{2u}$ is straight or branched alkylene, $R^{17}$ is $C_1$–$C_6$ straight alkyl, E is hydrogen or —$OR^{18}$ (wherein $R^{18}$ is $C_1$–$C_{12}$ acyl, $C_7$–$C_{15}$ aroyl or $R^2$ (wherein $R^2$ represents the same meaning as described above), the formula represents d-isomer, l-isomer and racemic body) or a pharmaceutically acceptable salt thereof.

The ophthalmic preparation according to the present invention has excellent therapeutic and preventive effects against various ophthalmic diseases such as glaucoma, hypertonia oculi or cataract.

BEST MODE FOR CARRYING OUT THE INVENTION

The ophthalmic preparation according to the present invention contains the $PGI_2$ derivative represented by the formula (I) as an effective ingredient. The $PGI_2$ derivative may be not only racemic body but also d-isomer or l-isomer.

Preferred examples of the $PGI_2$ derivatives include beraprost and salts thereof. The salts are pharmaceutically acceptable salts including alkaline metal salts such as sodium salt and potassium salt; alkaline earth metal salts such as magnesium salt and calcium salt; primary, secondary or tertiary ammonium salt; and basic amino acid. Preferred examples of the $PGI_2$ derivative also include Compounds 2 to 6 described in the examples described below.

The above-described $PGI_2$ derivatives per se employed in the ophthalmic preparation according to the present invention, as well as production processes thereof are known and described in, for example, U.S. Pat. No. 4,474,802.

By adding a cyclodextrin to the ophthalmic preparation containing the above-described $PGI_2$ derivative or a salt thereof, ophthalmic topical irritation, such as conjunctival hyperemia, chemosis or abnormal egesta, which is observed when a high concentration of $PGI_2$ derivative is applied may be prevented. Further, by adding a vasoconstrictor to the ophthalmic preparation containing the $PGI_2$ derivative, the ophthalmic topical irritation which is a side effect may be prevented without adding a cyclodextrin. By adding a vasoconstrictor to an ophthalmic preparation containing a cyclodextrin, the ophthalmic topical irritation may be better prevented.

Examples of the cyclodextrin include α-cyclodextrin, β-cyclodextrin, γ-cyclodextrin, dimethyl-β-cyclodextrin, trimethyl-β-cyclodextrin, hydroxypropyl-β-cyclodextrin, glucosyl-cyclodextrin, maltosyl-cyclodextrin and the like. Examples of the vasoconstrictor include naphazoline hydrochloride, naphazoline nitrate, tetrahydrozoline hydrochloride, phenylephrine hydrochloride and the like.

The concentration of the $PGI_2$ derivative or a salt thereof used in the present invention varies depending on the ophthalmic disease and any concentration may be employed as long as its effect is exhibited. Thus, although the concentration is not restricted, a concentration of 0.0001 to 1.0 wt % (in the present specification, all "%" means weight/volume % unless otherwise specified) is preferred. The concentrations of the cyclodextrin and vasoconstrictor vary depending on the concentration of the $PGI_2$ derivative or the salt thereof. In cases where the concentration of the $PGI_2$ derivative or the salt thereof is not more than 0.001%, ophthalmic topical irritation is not exhibited, so that there is no need to add a cyclodextrin or a vasoconstrictor. In cases where the concentration of the $PGI_2$ derivative or the salt thereof is not less than 0.003%, the cyclodextrin and/or the vasoconstrictor may be added in an amount by which ophthalmic topical irritation may be prevented. Although the concentrations are not restricted, usually, the concentration of the cyclodextrin is preferably 0.001 to 10.0%, and the concentration of the vasoconstrictor is preferably 0.0005 to 0.1%.

The ophthalmic preparation according to the present invention may not only be dropped or applied to cornea or conjunctiva, but also be injected into corps or anterior chamber. The effective ingredient may be blended with an ophthalmic ointment base such as petrolatum, liquid paraffin and Macrogold; fatty emulsion base such as soybean oil, egg yolk lecithin and soybean lecithin; isotonic agent such as sodium chloride, potassium chloride and glycerin; buffer such as borate buffer, phosphate buffer, citrate buffer and acetate buffer; stabilizer such as sodium edetate, sodium sulfite, propylene glycol, polyoxyethylene (20) sorbitan monoleate (polysorbate 80) and polyvinylpyrrolidone; viscosity increaser such as polyvinyl alcohol, carboxymethyl cellulose, hydroxyethyl cellulose and sodium chondroitin sulfate; pH regulator such as sodium hydroxide and hydrochloric acid; and antiseptic such as benzalkonium chloride, chlorobutanol, methylparaben and propylparaben.

The administration dose of the ophthalmic preparation according to the present invention may be appropriately selected depending on the type of disease, symptom, and purpose of administration. Usually, about 5 μl to 200 μl per one time is administered one to five times a day.

The ophthalmic preparation according to the present invention has an activity to decrease ocular tension, and has therapeutic and preventive effects for various ophthalmic diseases. Especially, it is effective as an agent for decreasing ocular tension, and thus exhibits excellent therapeutic and preventive effects against glaucoma, hypertonia oculi or postoperative hypertonia oculi. Further, it has an excellent therapeutic and preventive effects against cataract.

EXAMPLES

The present invention will now be described in more detail by way of examples and test examples. It should be noted that the ophthalmic preparation according to the present invention is not restricted to the prescriptions described in the examples.

| Formulation Example 1 | |
|---|---|
| Beraprost | 0.0005 g |
| White petrolatum | 77.0 g |
| Liquid paraffin | 22.96 g |
| Methylparaben | 0.0265 g |
| Propylparaben | 0.013 g |
| Total | 100.0 g |

| Formulation Example 2 | |
|---|---|
| Beraprost | 0.001 g |
| Purified Soybean Oil | 10.0 g |
| Purified Egg Yolk Lecithin | 1.2 g |
| Conc. glycerin | 2.5 g |
| Sodium hydroxide or diluted hydrochloric acid | Amount necessary for adjusting pH |
| Water for injection | Balance |
| Total | 100.0 ml |

| Formulation Example 3 | |
|---|---|
| Sodium beraprost | 0.001 g |
| Sodium chloride | 0.9 g |
| Water for injection | Balance |
| Total | 100.0 ml |

| Formulation Example 4 | |
|---|---|
| Sodium beraprost | 0.001 g |
| Boric acid | 0.02 g |
| Borax | 1.7 g |
| Chlorobutanol | 0.35 g |
| Sterilized Purified Water | Balance |
| Total | 100.0 ml |

| Formulation Example 5 | |
|---|---|
| Sodium beraprost | 0.003 g |
| β-cyclodextrin | 0.3 g |
| Sodium chloride | 0.9 g |
| Sterilized Purified Water | Balance |
| Total | 100.0 ml |

| Formulation Example 6 | |
|---|---|
| Sodium beraprost | 0.01 g |
| α-cyclodextrin | 0.8 g |
| Sodium dihydrogen phosphate (dodecahydrate) | 1.0 g |
| Sodium dihydrogen phosphate (anhydride) | 0.2 g |
| Sodium chloride | 0.6 g |
| Chlorobutanol | 0.4 g |
| Sterilized Purified Water | Balance |
| Total | 100.0 ml |

| Formulation Example 7 | |
|---|---|
| Sodium beraprost | 0.01 g |
| Tetrahydrozoline hydrochloride | 0.1 g |
| Boric acid | 2.0 g |
| Borax | 0.1 g |
| Benzalkonium chloride | 0.001 g |
| Sterilized Purified Water | Balance |
| Total | 100.0 ml |

| Formulation Example 8 | |
|---|---|
| Sodium beraprost | 0.05 g |
| Dimethyl-β-cyclodextrin | 3.0 g |
| Boric acid | 0.4 g |
| Borax | 1.7 g |
| Chlorobutanol | 0.4 g |
| Sterilized Purified Water | Balance |
| Total | 100.0 ml |

| Formulation Example 9 | |
|---|---|
| Sodium beraprost | 0.05 g |
| γ-cyclodextrin | 3.0 g |
| Boric acid | 2.0 g |
| Borax | 0.1 g |
| Benzalkonium chloride | 0.002 g |
| Sterilized Purified Water | Balance |
| Total | 100.0 ml |

| Formulation Example 10 | |
|---|---|
| Sodium beraprost | 0.1 g |
| Hydroxypropyl-β-cyclodextrin | 3.0 g |
| Naphazoline hydrochloride | 0.03 g |
| Sodium dihydrogen phosphate (dodecahydrate) | 1.0 g |
| Sodium dihydrogen phosphate (anhydride) | 0.2 g |
| Sodium edetate | 0.01 g |
| Sodium chloride | 0.6 g |
| Benzalkonium chloride | 0.002 g |
| Sterilized Purified Water | Balance |
| Total | 100.0 ml |

Test Example 1

Action to Decrease Ocular Tension

Activities of test compounds were tested using 2–3 New Zealand White Rabbits per group, whose body weights were 2–3.5 kg. As the test compounds, Compound 1 (sodium beraprost) to Compound 6 shown in Table 1 were used. The symbols $R^1$, E, B and Y in Table 1 indicate the same meanings as in Formula (I).

TABLE 1

| Compound 1 | $R^1$ | $COON_a$ |
|---|---|---|
| (Sodium beraprost) | E | ''''''OH |
| | B | 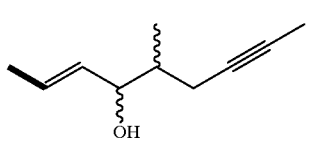 |
| Compound 2 | Y | H |
| | $R^1$ | $COOCH_3$ |

TABLE 1-continued

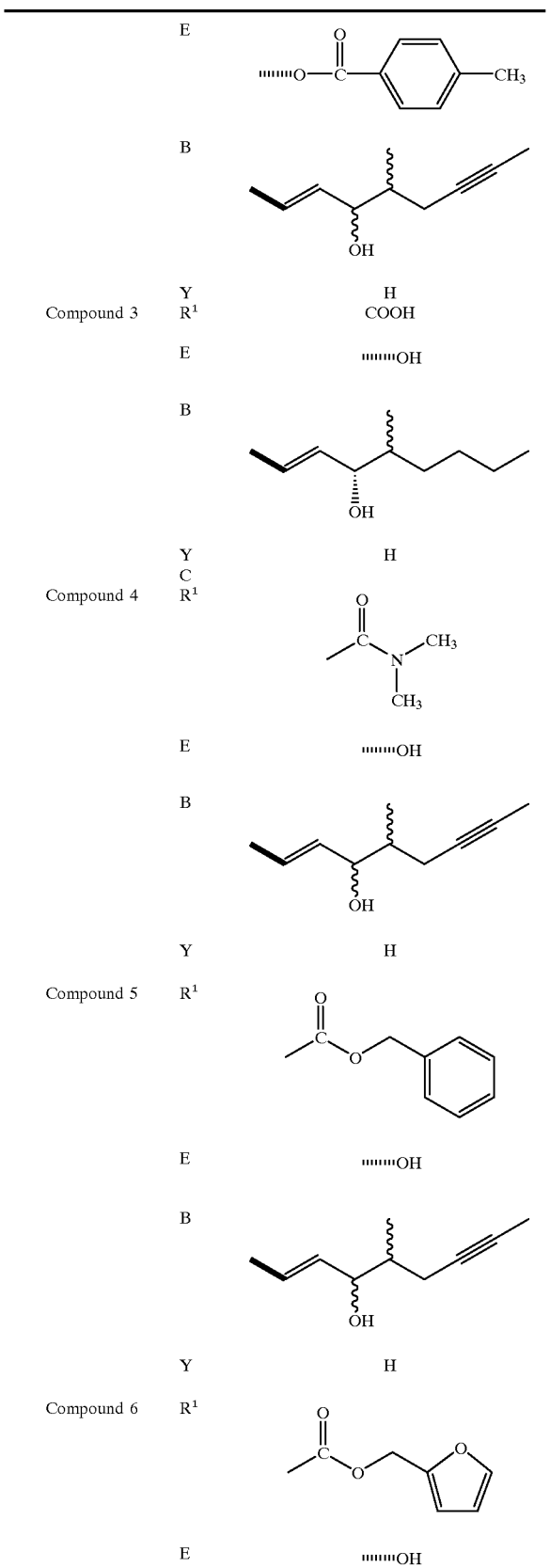

| | | |
|---|---|---|
| Compound 3 | Y<br>R[1]<br>E | H<br>COOH<br>''''''OH |
| | B | |
| Compound 4 | Y<br>C<br>R[1]<br>E | H<br><br><br>''''''OH |
| | B | |
| Compound 5 | Y<br>R[1]<br><br>E | H<br><br><br>''''''OH |
| | B | |
| Compound 6 | Y<br>R[1]<br><br>E | H<br><br><br>''''''OH |

TABLE 1-continued

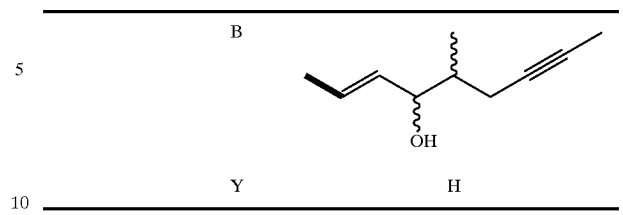

| Y | H |
|---|---|

The test compound was dropped into one eye and 30 μl of solvent was dropped to the other eye. The ocular tensions up to 4 hours or 6 hours from the administration of the compounds were measured with time with a pneumatic ophthalmotonometer (NIPPON ALCON). When measuring the ocular tension, 4% oxybuprocaine hydrochloride was dropped to the eyes as a surface anesthetic. Compound 1 was dissolved in 100 mM phosphate buffer and other compounds were dissolved in 2% polyoxyethylene(20)sorbitan monoleate, and the solutions were dropped to the eyes. The results are shown in Table 2.

TABLE 2

| Compound | Concentration | Maximum Decrease in Ocular Tension (mmHg) |
|---|---|---|
| Compound 1 (Sodium beraprost) | 0.03% | 4.7 |
| Compound 2 | 0.01% | 4.2 |
| Compound 3 | 0.01% | 2.8 |
| Compound 4 | 0.01% | 1.7 |
| Compound 5 | 0.01% | 6.5 |
| Compound 6 | 0.01% | 3.8 |

From the above-described results, it was proved that the ophthalmic preparations according to the present invention have activities to decrease ocular tension.

Test Example 2

To confirm activity of sodium beraprost to decrease ocular tension, a test was carried out using white male rabbits. Sodium beraprost was dissolved in physiological saline to a concentration shown in Table 2 below, and the obtained solution was dropped to the eyes of white male rabbits in an amount of 50 μl per time. Under anesthesia by dropping 4% oxybuprocaine hydrochloride to the eyes, ocular tension was measured with time. The results are shown in Table 3.

TABLE 3

| Concentration of Sodium beraprost | Number of Rabbits | Before Instillation (mmHg) | Ocular Tension after Instillation (mmHg) | | |
|---|---|---|---|---|---|
| | | | 1 hr | 2 hr | 3 hr |
| 0% | 12 | 16.3 | 16.5 | 17.1 | 17.4 |
| 0.001% | 6 | 16.2 | 14.3 | 14.3 | 14.5 |
| 0.003% | 6 | 16.5 | 14.0 | 13.8 | 14.0 |
| 0.01% | 12 | 16.6 | 15.2 | 13.8 | 13.3 |

As shown in Table 3, activity of sodium beraprost to decrease ocular tension was observed at a very low concentration of as low as 0.001%. Irritation of eye mucosa was not substantially observed at concentrations not more than 0.001%, while it was observed at concentrations not lower than 0.003%.

Test Example 3

The effects of cyclodextrins and a vasoconstrictor to prevent irritation of eye mucosa caused by sodium beraprost were tested using white male rabbits. As representative examples of cyclodextrins, α-cyclodextrin (αCyD), β-cyclodextrin (βCyD), γ-cyclodextrin (γCyD), hydroxypropyl-β-cyclodextrin (HPβCyD) and dimethyl-β-cyclodextrin (DMβCyD) were used, and as a representative example of vasoconstrictors, naphazoline hydrochloride (NZH) was used.

Sodium beraprost (BPS) was dissolved in physiological saline and the cyclodextrin or vasoconstrictor was dissolved therein to prepare test compositions. Each of the test compositions was dropped to eyes of white male rabbits in an amount of 50 µl per time, and the irritation of eye mucosa was observed with time and evaluated based on the scores given according to the following criteria:

|  | Scores |
|---|---|
| (A) Flare of conjunctiva | |
| Normal (no congestion) | 0 |
| Accentuation of congestion | 1 |
| Congestion in deep red color is observed in large area and blood vessels are hardly distinguished | 2 |
| (B) Chemosis of conjunctiva | |
| Normal (no chemosis) | 0 |
| Accentuation of chemosis | 1 |
| Chemosis accompanying partial evagination of eyelid | 2 |
| (C) Egesta | |
| Normal amount | 0 |
| Abnormal amount | 1 |
| Eyelid and eyelash were wetted | 2 |
| Evaluation (A) + (B) + (C) | |

As shown in Table 4, in rabbits who received 0.01% sodium beraprost, conjunctival hyperemia, chemosis of conjunctiva and abnormality in egesta were observed. However, with the test compounds to which the cyclodextrin or the vasoconstrictor was blended, irritation of eye mucosa was not substantially observed. As for the activity to decrease ocular tension shown in Table 5, the activity was not influenced by the cyclodextrin or the vasoconstrictor, and activity to decrease ocular tension was observed.

TABLE 4

| Test Drug | NOR* | Average Score before Instillation | Score after Instillation 1 hr | 2 hr | 3 hr |
|---|---|---|---|---|---|
| Physiological Saline | 6 | 0 | 0 | 0 | 0 |
| 0.01% BPS | 6 | 0 | 1.2 | 3.2 | 3.2 |
| 0.01% BPS + 1.8% α CyD | 6 | 0 | 0.2 | 0.2 | 0 |
| 0.01% BPS + 1.8% β CyD | 6 | 0 | 0.2 | 0 | 0 |
| 0.01% BPS + 1.8% γ CyD | 6 | 0 | 0 | 0.2 | 0 |
| 0.01% BPS + 1.8% HP β CyD | 6 | 0 | 0.2 | 0 | 0 |
| 0.01% BPS + 1.8% DM β CyD | 6 | 0 | 0 | 0 | 0 |
| 0.01% BPS + 0.01% NZH | 6 | 0 | 0 | 0.2 | 0.2 |

*Number of Rabbits

TABLE 5

| Test Drug | NOR* | Average Score before Instillation | Score after Instillation 1 hr | 2 hr | 3 hr |
|---|---|---|---|---|---|
| Physiological Saline | 6 | 16.2 | 16.7 | 16.7 | 17.3 |
| 0.01% BPS | 6 | 16.5 | 15.3 | 13.2 | 13.5 |
| 0.01% BPS + 1.8% α CyD | 6 | 16.0 | 14.3 | 13.5 | 14.0 |
| 0.01% BPS + 1.8% β CyD | 6 | 16.3 | 14.8 | 13.7 | 14.2 |
| 0.01% BPS + 1.8% γ CyD | 6 | 16.3 | 14.5 | 14.0 | 14.5 |
| 0.01% BPS + 1.8% H β CyD | 6 | 16.0 | 14.5 | 13.5 | 14.2 |
| 0.01% BPS + 1.8% D β CyD | 6 | 16.3 | 15.0 | 14.0 | 14.0 |
| 0.01% BPS + 0.01% NZH | 6 | 16.7 | 15.7 | 14.0 | 13.7 |

*Number of Rabbits

Test Example 4

To confirm the potential of sodium beraprost as a drug for cataract, crystalline lenses of rats were cultured in a culture medium containing 50 mM galactose and sodium beraprost for 48 hours, and the wet weight of each crystalline lens was measured. The content of reduced glutathione (GSH) in each crystalline lens was also measured. The results are shown in Tables 6 and 7.

TABLE 6

| Test Group Galactose (mM) | BPS (%) | Number of Cases | Wet Weight (mg) | Ratio of Inhibition of Swelling (%) |
|---|---|---|---|---|
| — | 0 | 5 | 28.5 | — |
| 50 | 0 | 5 | 33.5 | — |
| 50 | 0.0004 | 5 | 32.2 | 26.0 |
| 50 | 0.0042 | 5 | 31.5 | 40.0 |
| 50 | 0.0420 | 5 | 28.3 | 104.0 |

TABLE 7

| Test Group Galactose (mM) | BPS (%) | Number of Cases | GSH Content (µ mol/g lens) | Ratio of Inhibition of Decrease in Content (%) |
|---|---|---|---|---|
| — | 0 | 5 | 4.58 | — |
| 50 | 0 | 5 | 1.78 | — |
| 50 | 0.0004 | 5 | 2.04 | 10.1 |
| 50 | 0.0042 | 5 | 2.91 | 44.0 |
| 50 | 0.0420 | 5 | 2.77 | 38.5 |

As shown in Table 6, when the lenses were cultured in a culture medium containing no galactose, swelling of the lenses was not substantially observed, while when the lenses were cultured in a culture medium containing a high concentration of galactose, swelling of about 18% was observed. On the other hand, when the lenses were cultured in a culture medium containing a high concentration of galactose and sodium beraprost, swelling of the lenses was inhibited dose-dependently. Further, as shown in Table 7, the amount of the reduced glutathione in the lenses was clearly decreased by culturing the lenses in a culture medium containing high concentration of galactose, and it was confirmed that sodium beraprost inhibits decrease in the reduced glutathione in the lenses.

From the above-described results, it was shown that the above-described $PGI_2$ derivatives such as beraprost are useful for various ophthalmic diseases. Further, an excellent effect was shown that the irritation of eye mucosa caused by high concentration of beraprost can be prevented by blending a cyclodextrin or a vasoconstrictor.

What is claimed is:

1. An ophthalmic preparation comprising an effective amount of a compound of a 4,8-inter-m-phenylene prostaglandin $I_2$ derivative of the formula (I):

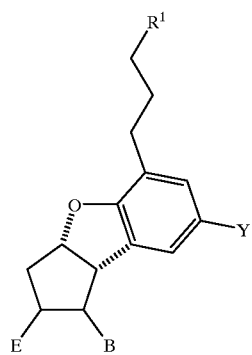

(I)

wherein $R^1$ is (A) $COOR^2$, wherein $R^2$ is
  1) hydrogen or a pharmaceutically acceptable cation,
  2) $C_1$–$C_{12}$ straight alkyl or $C_3$–$C_{14}$ branched alkyl,
  3) —Z—$R^3$, wherein Z is a valence bond or straight or branched alkylene represented by $C_tH_{2t}$ wherein t is an integer of 1 –6, $R^3$ is $C_3$–$C_{12}$ cycloalkyl or $C_3$–$C_{12}$ cycloalkyl substituted with 1 to 3 $R^4$ wherein $R^4$ is hydrogen or $C_1$–$C_5$ alkyl,
  4) —$(CH_2CH_2O)_nCH_3$, wherein n is an integer of 1–5,
  5) —Z—$Ar^1$, wherein Z represents the same meaning as described above, $Ar^1$ is phenyl, α-naphthyl, β-naphthyl, 2-pryidyl, 3-pyridyl, 4-pyridyl, α-furyl, β-furyl, α-thienyl, β-thienyl or substituted phenyl, wherein the substituent is at least one selected from the group consisting of chlorine, bromine, fluorine, iodine, trifluoromethyl, $C_1$–$C_4$ alkyl, nitro, cyano, methoxy, phenyl, phenoxy, p-acetamidobenzamide, —CH=N—NH—C(=O)—$NH_2$, —NH—C(=O)—Ph, —NH—C(=O)—$CH_3$ and —NH—C(=O)—$NH_2$—,
  6) —$C_tH_{2t}COOR^4$, wherein $C_tH_{2t}$ and $R^4$ represent the same meanings as described above,
  7) —$C_tH_{2t}N(R^4)_2$, wherein $C_tH_{2t}$ and $R^4$ represent the same meanings as described above,
  8) —$CH(R^5)$—C(=O)—$R^6$, wherein $R^5$ is hydrogen or benzoyl, $R^6$ is phenyl, p-bromophenyl, p-chlorophenyl, p-biphenyl, p-nitrophenyl, p-benzamidephenyl or 2-naphthyl,
  9) —$C_pH_{2p}$—W—$R^7$, wherein W is —CH=CH—, —CH=$CR^7$— or —C≡C—, $R^7$ is hydrogen, $C_1$–$C_{30}$ straight or branched alkyl or aralkyl, p is an integer of 1–5, or
  10) —$CH(CH_2OR^8)_2$, wherein $R^8$ is $C_1$–$C_{30}$ alkyl or acyl (B) —$CH_2OH$ (C) —C(=O)N$(R^9)_2$, wherein $R^9$ is hydrogen, $C_1$–$C_{12}$ straight alkyl, $C_3$–$C_{12}$ branched alkyl, $C_3$–$C_{12}$ cycloalkyl, $C_4$–$C_{13}$ cycloalkylalkylene, phenyl, substituted phenyl, wherein the definition of the substituents are the same as (A)5) described above, $C_7$–$C_{12}$ aralkyl or —$SO_2R^{10}$, wherein $R^{10}$ is $C_1$–$C_{10}$ alkyl, $C_3$–$C_{12}$ cycloalkyl, phenyl, substituted phenyl, wherein the definition of the substituents are the same as (A)5) described above, or $C_7$–$C_{12}$ aralkyl, with the proviso that although the two $R^9$ may be the same or different, when one is —$SO_2R^{10}$, the other $R^9$ is not —$SO_2R^{10}$, or (D) —$CH_2THP$, wherein THP represents tetrahydropyranyl, Y is hydrogen, $C_1$–$C_4$ alkyl, chlorine, bromine, fluorine, formyl, methoxy or nitro, B is —X—C$(R^{11})(R^{12})OR^{13}$, wherein $R^{11}$ is hydrogen or $C_1$–$C_4$ alkyl, $R^{13}$ is hydrogen, $C_1$–$C_{14}$ acyl, $C_6$–$C_{15}$ aroyl, tetrahydropyranyl, tetrahydrofuranyl, 1-ethoxyethyl or t-butyl, X is
  1) —$CH_2$—$CH_2$—,
  2) —CH=CH—, or
  3) —C≡—C—, $R^{12}$ is
  1) $C_1$–$C_{12}$ straight alkyl or $C_3$–$C_{14}$ branched alkyl,
  2) —Z—$AR^2$, wherein Z represents the same meaning as described above, $Ar^2$ represents phenyl, α-naphthyl, β-naphthyl or phenyl substituted with at least one selected from the group consisting of chlorine, bromine, fluorine, iodine, trifluoromethyl, $C_1$–$C_4$ alkyl, nitro, cyano, methoxy, phenyl and phenoxy,
  3) —$C_tH_{2t}OR^{14}$, wherein $C_tH_{2t}$ represents the same meaning as described above, $R^{14}$ is $C_1$–$C_6$ straight alkyl, $C_3$–$C_6$ branched alkyl, phenyl or substituted phenyl substituted with at least one selected from the group consisting of chlorine, bromine, fluorine, iodine, trifluoromethyl, $C_t$–$C_4$ alkyl, nitro, cyano, methoxy, phenyl and phenoxy, cyclopentyl, cyclohexyl, or cyclopentyl or cyclohexyl substituted with 1 to 4 $C_1$–$C_4$ straight alkyl,
  4) —Z—$R^3$, wherein Z and $R^3$ represent the same meanings as described above,
  5) —$C_tH_{2t}$—CH=C$(R^{15})R^{16}$, wherein $C_tH_{2t}$ represents the same meaning as described above, $R^{15}$ and $R^{16}$ independently represent hydrogen, methyl, ethyl, propyl or butyl, or
  6) —$C_uH_{2u}$—C≡C—$R^{17}$, wherein u is an integer of 1–7, $C_uH_{2u}$ is straight or branched alkylene, $R^{17}$ is $C_1$–$C_6$ straight alkyl, E is hydrogen or —$OR^{18}$, wherein $R^{18}$ is $C_1$–$C_{12}$ acyl, $C_7$–$C_{15}$ aroyl or $R^2$, wherein $R^2$ represents the same meaning as described above, the formula represents d-isomer, l-isomer or a racemic mixture, or a pharmaceutically acceptable salt thereof; and an effective amount of a cyclodextrin.

2. The ophthalmic preparation according to claim 1, further comprising an effective amount of a vasoconstrictor.

3. The ophthalmic preparation according to claim 1, wherein the cyclodextrin is selected from the group consisting of α-cyclodextrin, β-cyclodextrin, γ-cyclodextrin, dimethyl-β-cyclodextrin, trimethyl-β-cyclodextrin, hydroxypropyl-β-cyclodextrin, glucosyl-cyclodextrin and maltosyl cyclodextrin.

4. The ophthalmic preparation according to claim 2, wherein the vasoconstrictor is selected from the group consisting of naphazoline hydrochloride, naphozoline nitrate, tetrahydrozoline hydrochloride and phenylephrine hydrochloride.

5. The ophthalmic preparation according to claim 1 wherein the cyclodextrin is present in a concentration of 0.001–10% by weight.

6. The ophthalmic preparation according to claim 2, wherein the vasoconstrictor is present in a concentration of 0.0005–0.1% by weight.

7. The method according to claim 1, wherein the patient has glaucoma.

8. The method according to claim 1, wherein the patient has hypertonia oculi.

9. The method according to claim 1, wherein the patient has postoperative hypertonia oculi.

10. A method for decreasing ocular tension which comprises applying to an eye of a patient in need of treatment an ophthalmic preparation comprising as an effective ingredient a 4,8-inter-m-phenylene prostaglandin $I_2$ derivative of the formula (I):

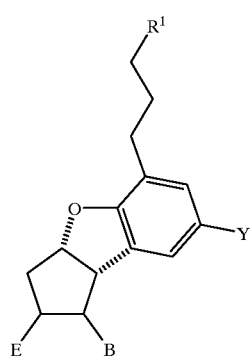

(I)

wherein $R^1$ is (A) $COOR^2$, wherein $R^2$ is
1) hydrogen or a pharmaceutically acceptable cation,
2) $C_1$–$C_{12}$ straight alkyl or $C_3$–$C_{14}$ branched alkyl,
3) —Z—$R^3$, wherein Z is a valence bond or straight or branched alkylene represented by $C_tH_{2t}$ wherein t is an integer of 1–6, $R^3$ is $C_3$–$C_{12}$ cycloalkyl or $C_3$–$C_{12}$ cycloalkyl substituted with 1 to 3 $R^4$ wherein $R^4$ is hydrogen or $C_1$–$C_5$ alkyl,
4) —$(CH_2CH_2O)_nCH_3$, wherein n is an integer of 1–5,
5) —Z—$Ar^1$, wherein Z represents the same meaning as described above, $Ar^1$ is phenyl, α-naphthyl, β-naphthyl, 2-pryidyl, 3-pyridyl, 4-pyridyl, α-furyl, β-furyl, α-thienyl, β-thienyl or substituted phenyl, wherein the substituent is at least one selected from the group consisting of chlorine, bromine, fluorine, iodine, trifluoromethyl, $C_1$–$C_4$ alkyl, nitro, cyano, methoxy, phenyl, phenoxy, p-acetamidobenzamide, —CH=N—NH—C(=O)—$NH_2$, —NH—C(=O)-Ph, —NH—C(=O) —$CH_3$ and —NH—C(=O) —$NH_2$,
6) —$C_tH_{2t}COOR^4$, wherein $C_tH_{2t}$ and $R^4$ represent the same meanings as described above,
7) —$C_tH_{2t}N(R^4)$, wherein $C_tH_{2t}$ and $R^4$ represent the same meanings as described above,
8) —CH($R^5$) —C (=O) —$R^6$, wherein $R^5$ is hydrogen or benzoyl, $R^6$ is phenyl, p-bromophenyl, p-chlorophenyl, p-biphenyl, p-nitrophenyl, p-benzamidephenyl or 2-naphthyl,
9) —$C_pH_{2p}$—W—$R^7$, wherein W is —CH=CH—, —CH=$CR^7$— or —C≡C—, $R^7$ is hydrogen, $C_1$–$C_{30}$ straight or branched alkyl or aralkyl, p is an integer of 1–5, or 10) —$CH(CH_2OR^8)_2$, wherein $R^8$ is $C_1$–$C_{30}$ alkyl or acyl (B) —$CH_2OH$ (C) —C(=O)$N(R^9)_2$, wherein $R^9$ is hydrogen, $C_1$–$C_{12}$ straight alkyl, $C_3$–$C_{12}$ branched alkyl, $C_3$–$C_{12}$ cycloalkyl, $C_4$–$C_{13}$ cycloalkylalkylene, phenyl, substituted phenyl, wherein the definition of the substituents are the same as (A)5) described above, $C_7$–$C_{12}$ aralkyl or —$SO_2R^{10}$, wherein $R^{10}$ is $C_1$–$C_{10}$ alkyl, $C_3$–$C_{12}$ cycloalkyl, phenyl, substituted phenyl, wherein the definition of the substituents are the same as (A)5) described above, or $C_7$–$C_{12}$ aralkyl, with the proviso that although the two $R^9$ may be the same or different, when one is —$SO_2R^{10}$, the other $R^9$ is not —$SO_2R^{10}$, or (D) —$CH_2OTHP$, wherein THP represents tetrahydropyranyl, Y is hydrogen, $C_1$–$C_4$ alkyl, chlorine, bromine, fluorine, formyl, methoxy or nitro, B is —X—C($R^{11}$) ($R^{12}$)$OR^{13}$, wherein $R^{11}$ is hydrogen or $C_1$–$C_4$ alkyl, $R^{13}$ is hydrogen, $C_1$–$C_{14}$ acyl, $C_6$–$C_{15}$ aroyl, tetrahydropyranyl, tetrahydrofuranyl, 1-ethoxyethyl or t-butyl, X is
1) —$CH_2$—$CH_2$—,
2) —CH=CH—, or
3) —C≡C—, $R^{12}$ is
1) $C_1$–$C_{12}$ straight alkyl or $C_3$–$C_{14}$ branched alkyl,
2) —Z—$AR^2$, wherein Z represents the same meaning as described above, $Ar^2$ represents phenyl, α-naphthyl, β-naphthyl or phenyl substituted with at least one selected from the group consisting of chlorine, bromine, fluorine, iodine, trifluoromethyl, $C_1$–$C_4$ alkyl, nitro, cyano, methoxy, phenyl and phenoxy,
3) —$C_tH_{2t}$ $OR^{14}$, wherein $C_tH_{2t}$ represents the same meaning as described above, $R^{14}$ is $C_1$–$C_6$ straight alkyl, $C_3$–$C_6$ branched alkyl, phenyl or substituted phenyl substituted with at least one selected from the group consisting of chlorine, bromine, fluorine, iodine, trifluoromethyl, $C_1$–$C_4$ alkyl, nitro, cyano, methoxy, phenyl and phenoxy, cyclopentyl, cyclohexyl, or cyclopentyl or cyclohexyl substituted with 1 to 4 $C_1$–$C_4$ straight alkyl,
4) —Z—$R^3$, wherein Z and R represent the same meanings as described above,
5) —$C_tH_{2t}$—CH=C($R^{15}$)$R^{16}$, wherein $C_tH_{2t}$ represents the same meaning as described above, $R^{15}$ and $R^{16}$ independently represent hydrogen, methyl, ethyl, propyl or butyl, or
6) —$C_uH_{2u}$—C≡C—R, wherein u is an integer of 1–7, $C_uH_{2u}$ is straight or branched alkylene, $R^{17}$ is $C_1$–$C_6$ straight alkyl, E is hydrogen or —$OR^{18}$, wherein $R^{18}$ is $C_1$–$C_{12}$ acyl, $C_7$–$C_{15}$ aroyl or $R^2$, wherein $R^2$ represents the same meaning as described above, the formula represents d-isomer, l-isomer or a racemic mixture, or a pharmaceutically acceptable salt thereof; and a pharmaceutically acceptable carrier suitable for application to an eye.

11. The method of claim 10, wherein said patient has glaucoma, hypertonia oculi or postoperative hypertonia oculi.

12. The method according to claim 10, wherein said 4,8-inter-m-phenylene derivative represented by the formula (I) is beraprost or a salt thereof.

13. The method according to claim 10, wherein said 4,8-inter-m-phenylene derivative represented by the formula (I) is one in which $R^1$ is —$COOCH_3$, E is

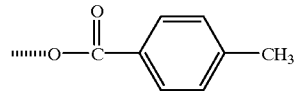

B is

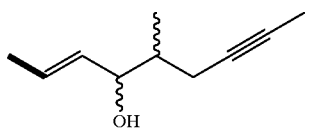

and Y is hydrogen.

14. The method according to claim 10, wherein said 4,8-inter-m-phenylene derivative represented by the formula (I) is one in which $R^1$ is —COOH, E is

IIIIIOH,

B is

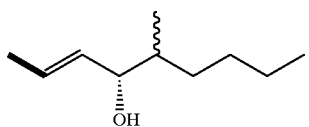

and Y is hydrogen.

15. The method according to claim 10, wherein said 4,8-inter-m-phenylene derivative represented by the formula (I) is one in which $R^1$ is

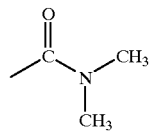

E is

IIIIIOH,

B is

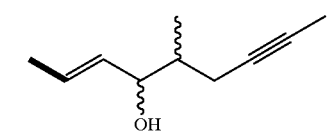

and Y is hydrogen.

16. The method according to claim 10, wherein said 4,8-inter-m-phenylene derivative represented by the formula (I) is one in which $R^1$ is

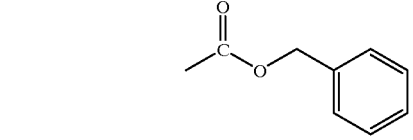

E is

IIIIIOH,

B is

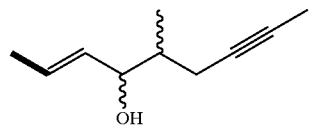

and Y is hydrogen.

17. The method according to claim 10, wherein said 4,8-inter-m-phenylene derivative represented by the formula (I) is one in which $R^1$ is

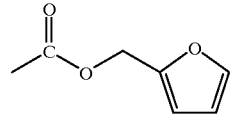

E is

IIIIIOH,

B is

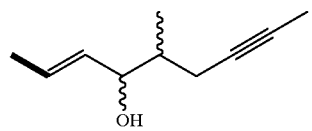

and Y is hydrogen.

* * * * *